US010357468B2

(12) United States Patent
Soares da Silva et al.

(10) Patent No.: US 10,357,468 B2
(45) Date of Patent: Jul. 23, 2019

(54) MEDICAMENTS FOR SLOWING PARKINSON'S DISEASE

(71) Applicant: BIAL—PORTELA & CA, S.A., Sao Mamede do Coronado (PT)

(72) Inventors: Patricio Manuel Vieira Araujo Soares da Silva, Sao Mamede do Coronado (PT); Jose Francisco da Costa de Pinho Rocha, Sao Mamede do Coronado (PT)

(73) Assignee: BIAL—PORTELA & CA, S.A., São Mamede do Coronado (PT)

( * ) Notice: Subject to any disclaimer, the term of this patent is extended or adjusted under 35 U.S.C. 154(b) by 0 days.

(21) Appl. No.: 15/528,886

(22) PCT Filed: May 27, 2015

(86) PCT No.: PCT/IB2015/000766
§ 371 (c)(1),
(2) Date: May 23, 2017

(87) PCT Pub. No.: WO2016/083875
PCT Pub. Date: Jun. 2, 2016

(65) Prior Publication Data
US 2017/0340593 A1  Nov. 30, 2017

(30) Foreign Application Priority Data

Nov. 28, 2014 (WO) .................. PCT/IB2014/003241

(51) Int. Cl.
| A61K 31/165 | (2006.01) |
| A61K 45/06 | (2006.01) |
| A61K 31/198 | (2006.01) |
| A61K 31/4439 | (2006.01) |
| A61K 31/00 | (2006.01) |

(52) U.S. Cl.
CPC .......... *A61K 31/198* (2013.01); *A61K 31/165* (2013.01); *A61K 31/4439* (2013.01); *A61K 45/06* (2013.01); *A61K 31/00* (2013.01)

(58) Field of Classification Search
None
See application file for complete search history.

(56) References Cited

U.S. PATENT DOCUMENTS

| 1,532,178 A | 4/1925 | Godbold |
| 3,647,809 A | 3/1972 | Reiter et al. |
| 4,065,563 A | 12/1977 | Narayanan et al. |
| 4,264,573 A | 4/1981 | Powell et al. |
| 4,386,668 A | 6/1983 | Parish |
| 4,963,590 A | 10/1990 | Backstrom et al. |
| 5,236,952 A | 8/1993 | Bernauer et al. |
| 5,476,875 A | 12/1995 | Bernauer et al. |
| 5,633,371 A | 5/1997 | Bernauer et al. |
| 5,705,703 A | 1/1998 | Bernauer et al. |
| 5,840,769 A | 11/1998 | Kolter et al. |
| 6,206,110 B1 | 3/2001 | Slaughter, Jr. et al. |
| 6,500,867 B1 | 12/2002 | Virkki et al. |
| 6,509,363 B2 | 1/2003 | Salituro et al. |
| 6,512,136 B1 | 1/2003 | Benes et al. |
| 6,660,753 B2 | 12/2003 | Van Wagenen et al. |
| 7,041,685 B2 | 5/2006 | Cai et al. |
| 7,112,595 B2 | 9/2006 | Wagenen et al. |
| 7,144,876 B2 | 12/2006 | Cai et al. |
| 7,317,029 B2 | 1/2008 | Cai et al. |
| 7,435,750 B2 | 10/2008 | Cai et al. |
| 7,553,964 B2 | 6/2009 | Liu et al. |
| 8,168,793 B2 | 5/2012 | Learmonth et al. |
| 8,524,746 B2 | 9/2013 | Learmonth et al. |
| 8,536,203 B2 | 9/2013 | Learmonth et al. |
| 8,907,099 B2 | 12/2014 | Learmonth et al. |
| 8,975,410 B2 | 3/2015 | Learmonth et al. |
| 9,126,988 B2 | 9/2015 | Russo et al. |
| 9,446,012 B2 | 9/2016 | Learmonth et al. |
| 9,550,759 B2 | 1/2017 | Learmonth et al. |
| 9,630,955 B2 | 4/2017 | Russo et al. |
| 2002/0012701 A1 | 1/2002 | Kolter et al. |
| 2003/0055085 A1 | 3/2003 | Wagenen et al. |
| 2004/0097555 A1 | 5/2004 | Ohkawa et al. |
| 2004/0138281 A1 | 7/2004 | Wikstrom et al. |
| 2004/0171645 A1 | 9/2004 | Bartoszyk et al. |
| 2006/0019956 A1 | 1/2006 | Green |
| 2006/0160812 A1 | 7/2006 | Schubert et al. |
| 2006/0173074 A1 | 8/2006 | Ellmen et al. |
| 2006/0257473 A1 | 11/2006 | Puranajoti |
| 2007/0013830 A1 | 1/2007 | Hayakawa |
| 2007/0026054 A1 | 2/2007 | Theobald et al. |

(Continued)

FOREIGN PATENT DOCUMENTS

| CN | 1340500 A | 3/2002 |
| CN | 1173926 C | 11/2004 |

(Continued)

OTHER PUBLICATIONS

Rocha et al., Effect of opicapone and entacapone upon levodopa pharmacokinetics during three daily levodopa administrations, ( 2014) Eur J Clin Pharmacol 70:1059-1071.*
Ferreira et al., Effect of opicapone multiple-dose regimens on levodopa pharmacokinetics, motor response, and erythrocyte-COMT activity in Parkinson's patients co-administered with levodopa/dopa-decarboxylase inhibitor, (Oct. 15, 2013) , Journal of Neurological Sciences vol. 333, p. e16, Abstract No. 1034.*
[No Author Listed] "[1,2,4]-oxadazolyl nitrocatechol derivatives" IP.com Journal, IP.com Inc., West Henrietta, NY, US, May 3, 2012. XP013150541.
[No Author Listed] COMT inhibitor definition from Wikipedia, retrieved from http://en.wikipedia.org/w/index.php?title=COMT_inhibitor&oldid=478541384, last accessed Jan. 31, 2014.

(Continued)

*Primary Examiner* — John D Ulm
(74) *Attorney, Agent, or Firm* — McCarter & English, LLP; Steven G. Davis; Wei Song (57) ABSTRACT

Opicapone, levodopa and an AADC inhibitor are described for use in slowing the progression of Parkinson's Disease.

21 Claims, 3 Drawing Sheets

(56) References Cited

U.S. PATENT DOCUMENTS

| | | |
|---|---|---|
| 2007/0048384 A1 | 3/2007 | Rosenberg et al. |
| 2007/0078133 A1 | 4/2007 | Liu et al. |
| 2007/0117165 A1 | 5/2007 | Presnell et al. |
| 2007/0219187 A1 | 9/2007 | Bessis et al. |
| 2007/0299110 A1 | 12/2007 | Gagliardi et al. |
| 2008/0051441 A1 | 2/2008 | Brown et al. |
| 2008/0071184 A1 | 3/2008 | Carter |
| 2008/0167286 A1 | 7/2008 | Gopalakrishnan et al. |
| 2008/0269236 A1 | 10/2008 | Ji et al. |
| 2009/0000437 A1 | 1/2009 | Johnson et al. |
| 2009/0054437 A1 | 2/2009 | Learmonth et al. |
| 2009/0111778 A1 | 4/2009 | Apodaca et al. |
| 2009/0162283 A1 | 6/2009 | Bando et al. |
| 2009/0227626 A1 | 9/2009 | Deraeve et al. |
| 2009/0312347 A1 | 12/2009 | Dahl et al. |
| 2010/0004284 A1 | 1/2010 | Farina et al. |
| 2010/0113529 A1 | 5/2010 | Learmonth et al. |
| 2010/0168113 A1 | 7/2010 | Learmonth et al. |
| 2010/0256193 A1 | 10/2010 | Cardoso de Vasconcelos et al. |
| 2010/0256194 A1 | 10/2010 | Cardoso de Vasconcelos et al. |
| 2011/0014282 A1 | 1/2011 | de Vasconcelos |
| 2011/0112301 A1 | 5/2011 | Learmonth et al. |
| 2011/0301204 A1 | 12/2011 | de Almeida et al. |
| 2012/0196904 A1 | 8/2012 | Learmonth et al. |
| 2013/0324578 A1 | 12/2013 | Soares Da Silva et al. |
| 2013/0331416 A1 | 12/2013 | Learmonth et al. |
| 2014/0024682 A1 | 1/2014 | Learmonth et al. |
| 2014/0045900 A1 | 2/2014 | Soares Da Silva et al. |
| 2014/0350057 A1 | 11/2014 | Russo et al. |
| 2015/0072977 A1 | 3/2015 | Learmonth et al. |
| 2015/0166519 A1 | 6/2015 | Learmonth |
| 2015/0359783 A1 | 12/2015 | de Vasconcelos et al. |
| 2016/0009699 A1 | 1/2016 | Learmonth et al. |
| 2016/0009700 A1 | 1/2016 | Russo et al. |

FOREIGN PATENT DOCUMENTS

| | | |
|---|---|---|
| DE | 3740383 A1 | 6/1988 |
| EP | 0237929 A1 | 9/1987 |
| EP | 0372654 A2 | 6/1990 |
| EP | 0462639 A1 | 12/1991 |
| EP | 0487774 A1 | 6/1992 |
| EP | 1167342 A1 | 1/2002 |
| EP | 1 845 097 A1 | 10/2007 |
| EP | 1 881 979 A1 | 1/2008 |
| FR | 1260080 A | 5/1961 |
| JP | H10-67651 A | 3/1998 |
| JP | 2002-020319 A | 1/2002 |
| JP | 2003-116966 A | 4/2003 |
| WO | 1993/13083 A1 | 7/1993 |
| WO | 00/37423 A1 | 6/2000 |
| WO | 01/12627 A1 | 2/2001 |
| WO | 2001/68083 A1 | 9/2001 |
| WO | 02/051442 A1 | 7/2002 |
| WO | 02/068417 A2 | 9/2002 |
| WO | 2002/096867 A2 | 12/2002 |
| WO | 2002/100826 A2 | 12/2002 |
| WO | 2004058163 A2 | 7/2004 |
| WO | 2005/013982 A1 | 2/2005 |
| WO | 2005/044797 A1 | 5/2005 |
| WO | 2005/105780 A2 | 11/2005 |
| WO | 2006/061697 A1 | 6/2006 |
| WO | 2006/071184 A1 | 7/2006 |
| WO | 2006/114400 A1 | 11/2006 |
| WO | 2006/129199 A1 | 12/2006 |
| WO | 2006/132914 A2 | 12/2006 |
| WO | 2007/013830 A1 | 2/2007 |
| WO | 2007034024 A2 | 3/2007 |
| WO | 2007/113276 A1 | 10/2007 |
| WO | 2007/117165 A1 | 10/2007 |
| WO | 2008/021388 A1 | 2/2008 |
| WO | 2008/094053 A1 | 8/2008 |
| WO | 2009/029632 A1 | 3/2009 |
| WO | 2010/014025 A1 | 2/2010 |
| WO | 2011/107653 A2 | 9/2011 |
| WO | 2012/107708 A1 | 8/2012 |

OTHER PUBLICATIONS

Al-Mousawi, S.M. et al., "Alkylazinylcarbonitriles as building blocks in heterocyclic synthesis: a route for the synthesis of 4-methyl-2-oxopyridines," Pharmazie, 54, 8, pp. 571-574 (1999).

Al-Omran, F. et al., "Heterocyclic Synthesis via Enaminones: Novel Synthesis of (1 H)-Pyridin-2-one, Pyrazolo [1 ,5-?]pyrimidine and Isoxazole Derivatives Incorporating a N-Methylphthalimide and Their Biological Evaluation", J. Heterocyclic Chem., 42, pp. 307-312 (2005).

Ansel et al., Pharmaceutical Dosage Forms and Drug Delivery Systems, 6th edition, 1995. pp. 192-203.

Bioavailability; published Feb. 2, 2011; retrieved from internet Apr. 7, 2016; https://en.wikipedia.org/w/index.php?title=Bioavailability&oldid=411623071>.

Bondvalli et al., "An Efficient Synthesis of Functionalized 2-Pyridones by Direct Route or via Amide/Enolate Ammonium Salt Intermediates", Synthesis, No. 7, pp. 1169-1174 (1999).

Bonifacio, M.J., et al., "Brain and peripheral pharmacokinetics of levodopa in the cynomolgus monkey following adminsitration of opicapone, a third generation nitrocatechol COMT inhibitor", Neuropharmacology, vol. 77, pp. 334-341 (2014).

Costa, R., et al., "Opicapone long-term efficacy and safety in Parkinson's disease BIPARK-II study: a one-year open-label follow-up", European Journal of Neurology, 21(1):171 (2014).

Davies, Ian W. et al., "A General [ 3+2+1] Annulation Strategy for the Preparation of Pyridine N-Oxides", Organic Letters, vol. 3, No. 2, pp. 209-211 (2001).

Dmitriyeva et al. "Features of the reaction of some 2-chloronicotinonitriles with hydroxylamine. Synthesis of 3-(1, 2, 4-oxadiazol-3yl)pyridines and their fragmentation under electron impact" IzvestiyaVysshikh UchehnykhZavedenii, Khimiya i Khimicheskaya Tekhnologiya, 2005, vol. 48, No. 11, pp. 15-17, CAPLUS Abstract, ON 145:103612.

Dutrow, B. "X-ray Powder Diffraction," excerpt, http://serc.carleton.edu/research_education/geochemsheets/techniques/XRD.html posted Aug. 2008, retrieved from Internet Archive Wayback Machine May 11, 2016.

English translation of JP 2003-116966.

EPO Search Report and Written Opinion—EP 06075343 Date of completion of the search Mar. 28, 2006, 5 pages.

Ferreira, J.J., et al., "Effect of opicapone multiple-dose regimens on levodopa pharmacokinetics, motor response, and erythrocyte-COMT activity in Parkinson's patients co-administered with levodopa/dopa-decarboxylase inhibitor", Journal of Neurological Sciences, vol. 333, p. e116 (2013), Abstract No. 1034.

Girges et al., (Chemical Papers (1992), 46(4), 272-277).

Grosset, D.G. et al., Parkinson's Disease, Clinician's Desk Reference, Manson Publishing, 2009, p. 62.

Howse, "Brocresine in Parkinson's disease, Action of a peripheral and central decarboxylase inhibitor in potentiating levodopa," Journal of Neurology, Neurosurgery, and Psychiatry, 1973,36, pp. 27-29.

International Preliminary Report on Patentability for PCT/PT2006/000020, dated Jan. 29, 2008.

International Preliminary Report on Patentability for PCT/PT2007/000016, dated Oct. 14, 2008.

International Preliminary Report on Patentability for PCT/PT2007/000043, dated Aug. 4, 2009.

International Preliminary Report on Patentability for PCT/PT2009/000044, dated Feb. 10, 2011.

International Search Report and Written Opinion for PCT/PT2006/000020, dated Nov. 8, 2006.

International Search Report and Written Opinion for PCT/PT2007/000016, dated Jul. 13, 2007,12 pages.

International Search Report and Written Opinion for PCT/PT2007/000043, dated Apr. 23, 2008.

International Search Report and Written Opinion for PCT/PT2009/000044, dated Nov. 16, 2009, 16 pages.

(56) References Cited

OTHER PUBLICATIONS

Ivanova, L.A., "Technology of dosage forms," Moscow, Medicine, vol. 2, 1991, pp. 223-224. English translation.
Kiss, L. E. et al., "Discovery of a long-acting, peripherally selective inhibitor of a catechol-O-methyltransferase" Journal of Medicinal Chemistry, American Chemical Society, US, vol. 53, No. 8, Apr. 22, 2010, pp. 3396-3411. XP002594266.
Korolkovas, A. "Essentials of Medicinal Chemistry", Development of Drugs, Second Edition, pp. 97-103 and 135-137 (1988).
Kristensen et al., "Granulation A Review on Pharmaceutical Wet-Granulation Drug Development and Industrial Pharmacy", 13(4 &5), 803-872 (1987).
Krogsgaard-Larsen, P. et al., "Textbook of Drug Design and Discovery", Third Edition, Table 14.3, pp. 426-427 (2002).
Learmonth, David., et al., "Chemical Synthesis and Characterization of Conjugates of a Novel Catechol-O-methyltransferase Inhibitor", Bioconjugate Chem., vol. 13, pp. 1112-1118, American Chemical Society, 2002.
Lees, A., et al., "Efficacy and safety of opicapone, a new COMT-inhibitor, for the treatment of motor fluctuations in Parkinson's Disease patients: BIPARK-II study", Journal of Neurological Sciences, vol. 333, p. e116 (2013), Abstract No. 1038.
Madopar, Instructions for use, found on-line Jun. 28, 2016; URL:http://www.webvidal.ru/2010/drug/LP_18271.htm; Feb. 2, 2011.
Marcoux, Jean-Francois et al., "A General Preparation of Pyridines and Pyridones via the Annulation of Ketones and Esters," J. Org. Chem, 66, pp. 4194-4199 (2001).
Morbus Parkinson, Stellenwert von COMT-Hemmern Bestatigt, May 3, 2004, 2 pages.
Nutt, John G., "Catechol-O-methyltransferase inhibitors for treatment of Parkinson's disease", Commentary, vol. 351, pp. 1221-1222, The Lancet, Apr. 1998.
Nutt, John G., et al., "Pharmacokinetics of Levodopa", Clinical Neuropharmacology, vol. 7, No. 1, pp. 35-49, Raven Press, 1984.
Parashos, S.A., et al., "Frequency, Reasons, and Risk Factors of Entacapone Discontinuation in Parkinson Disease", Clin. Neuropharmacol, (2004), vol. 27, No. 3, pp. 119-123.
Pedrosa, R., et al., "Oxidative and non-oxidative mechanisms of neuronal cell death and apoptosis by L-3,4-dihydroxyphenylalanine (L-DPOA) and dopamine", British Journal of Pharmacology, vol. 137, pp. 1305-1313, Nature Publishing Group, 2002.
Poulain, R.F. et al., "Parallel synthesis of 1, 2, 4-oxadiazoles from carboxylic acids using an improved, uranium-based, acitvation", Tetrahedron Letters 42: 1495-1498 (2001).
Rasenack, N et al., "Micron-size drug particles: common and novel micronization techniques", Pharmaceutical Development and Technology, New York, NY, US, vol. 9, No. 1., Jan. 1, 2004, pp. 1-13. XP009055393.
Reches, A., et al., "3-O-Methyldopa inhibits rotations induced by levodopa in rats after unilateral destruction of the nigrostnatal pathway", Neurology, (1982), vol. 32, No. 8, pp. 887-888.
Smith, K.S., et al., "In Vitro Metabolism of Tolcapone to Reactive Intermediates: Relevance to Tolcapone Liver Toxicity", Chem. Res. Toxicol., (2003), vol. 16, pp. 123-128.
Soares-Da-Silva, P. et al., "The O-methylated derivative of L-DOPA, 3-O-methyl-L-DOPA, fails to inhibit neuronal and non-neuronal aromatic L-amino acid decarboxylase", Brain Research, (2000), 863, pp. 293-297.
Tervo, Anu J., et al., "A structure-activity relationship study of catechol-O-methyltransferase inhibitors combining molecular docking and 3D QSAR methods", Journal of Computer-Aided Molecular Design, vol. 17, pp. 797-810, Kluwer Academic Publishers, 2003.
Tohgi, Hideo, et al., "The significance of 3-O-methyldopa concentrations in the cerebrospinal fluid in the pathogenesis of wearing-off phenomenon in Parkinson's Disease", Neuroscience Letters, vol. 132, pp. 19-22, Elsevier Scientific Publishers Ireland Lt (1991).
Vieira-Coelho, M.A., et al., "Effects of tolcapone upon soluble and membrane-bound brain and liver catechol-O-methyltransferase", Brain Research, vol. 821, pp. 69-78, Elsevier Science B.V., 1999.

\* cited by examiner

Figure 1:
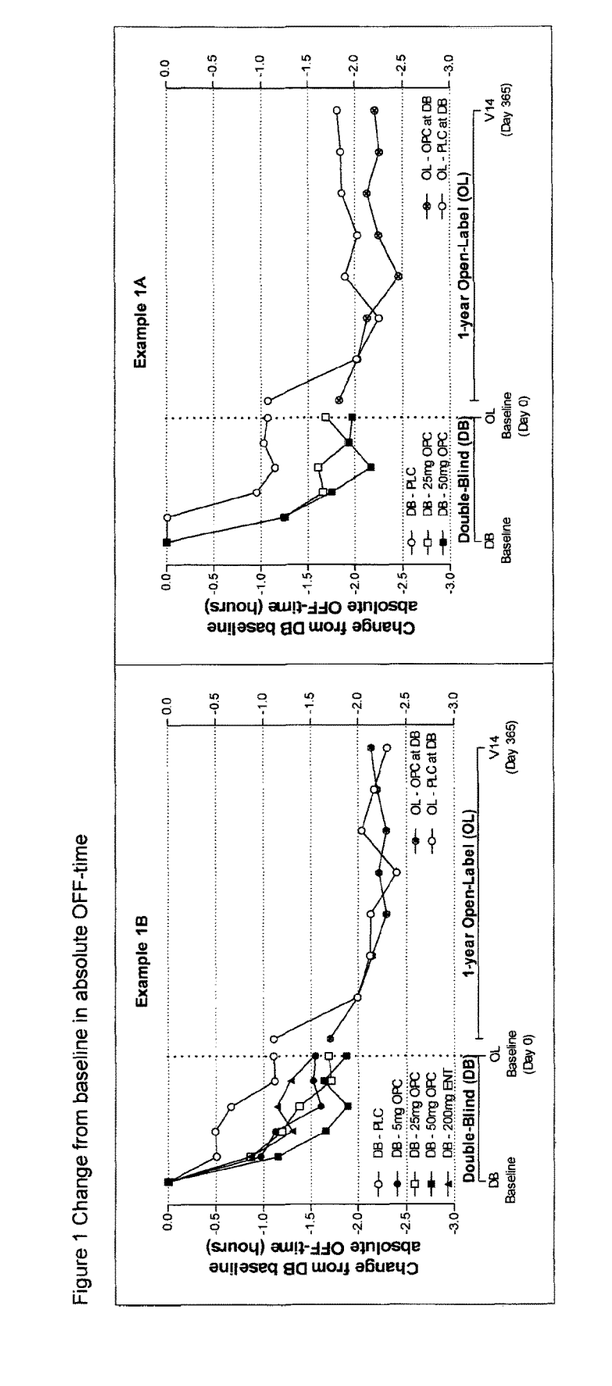

Figure 1 Change from baseline in absolute OFF-time

Figure 2:
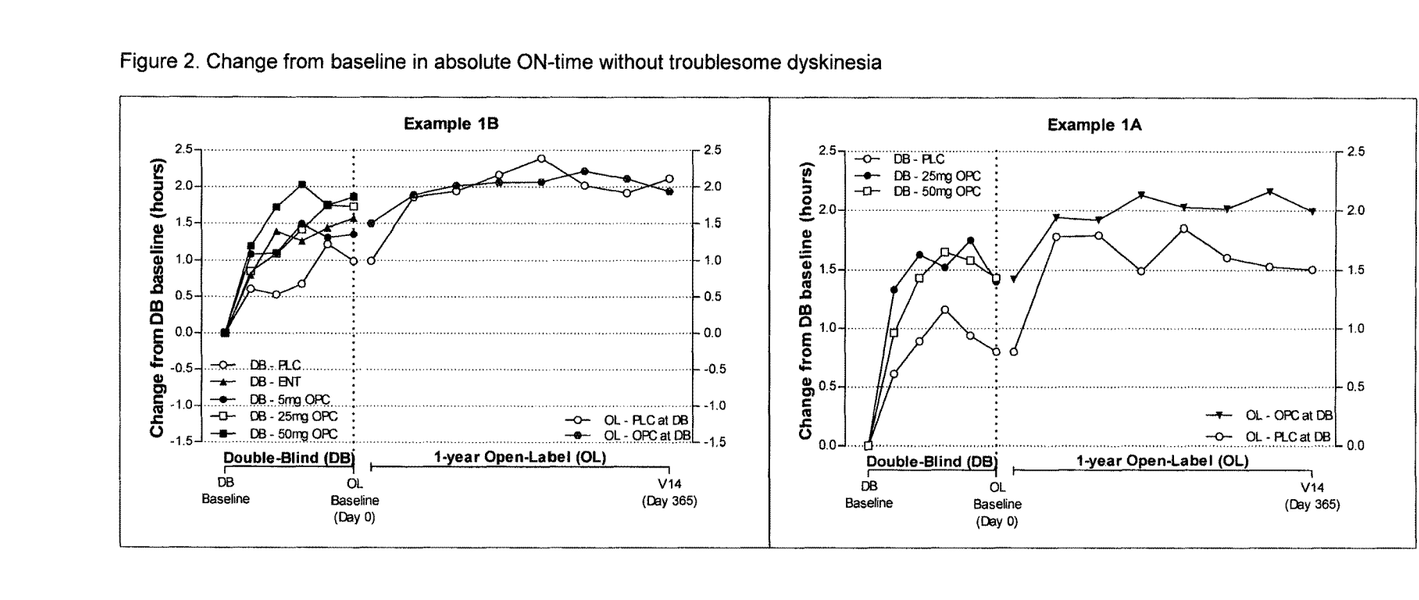

Figure 2. Change from baseline in absolute ON-time without troublesome dyskinesia Figure 3 Study Design

MEDICAMENTS FOR SLOWING PARKINSON'S DISEASE

CROSS-REFERENCE TO RELATED APPLICATIONS

This application is a U.S. national stage filing under 35 U.S.C. § 371(c), of International Application No. PCT/IB2015/000766, filed on May 27, 2015, which claims foreign priority of International Application No. PCT/IB2014/003241, filed on Nov. 28, 2014. The entire contents of each of the foregoing applications are incorporated herein by reference.

FIELD OF INVENTION

The present invention relates to the use of medicaments to slow the progression of Parkinson's Disease (PD). More particularly, this invention relates to the use of opicapone and levodopa (L-DOPA) optionally together with an amino acid decarboxylase inhibitor (AADC inhibitor, AADCi) to slow the progression of PD.

BACKGROUND OF THE INVENTION

PD is characterised by loss of dopamine-generating cells in a region of the brain known as the substantia nigra. Treatment of PD therefore focuses on increasing dopamine levels in the brain, and the various dopaminergic drugs used in PD treatment aim to either replace dopamine or prevent its degradation.

A number of PD symptoms arise from decreased dopamine levels, and can be classified into motor and non-motor symptoms. The group of motor symptoms include i) resting tremor that affects, for example the arms, legs and jaw; ii) a slowness of movement or bradykinesia, and iii) lack of movement/rigidity or akinesia. In addition, the motor symptoms experienced by PD sufferers also include problems with posture (instability thereof) and gait.

Non-motor symptoms of PD patients include neuropsychiatric symptoms, sleep disorders and wakefulness, and autonomic symptoms.

PD is a heterogeneous disorder with a clinical presentation that varies substantially from patient to patient. Current clinical guidelines (EMA 2012 guideline (EMA/CHMP/330418/2012 rev. 2) provide that the clinical diagnosis of PD requires bradykinesia and at least one of the following: resting tremor, muscular rigidity and postural reflex impairment (core symptoms).

PD is characteristically a progressive neurodegenerative disorder. The progress of the disease is apparent from the response of the PD patient to dopaminergic therapy over time. In the initial stages of the disease the principal symptoms such as tremor, bradykinesia, and rigidity can usually be ameliorated by dopaminergic therapies such as dopamine agonists, monoamine oxidase inhibitors or levodopa. None of these conventional treatments are considered to slow the progression of PD but can help patients control at least some motor symptoms. PD patients are said to be in the ON state when they are free, or largely free, of the PD symptoms described above. In contrast, PD patients are said to be in the OFF state when they are not in the ON state, for example when they exhibit PD symptoms.

The symptoms of PD may be ameliorated by treatment with dopamine agonists, monoamine oxidase inhibitors or levodopa. None of these conventional treatments are considered to slow the progression of PD but all can help at least some patients control the symptoms of the disease, such as tremor.

After this initial disease stage, the efficacy of the dopaminergic therapy reduces and "wearing off" or "end of dose" deterioration (such as motor fluctuations) occurs in most patients, as well as dyskinesia (the phenomenon of drug-induced involuntary movements including chorea and dystonia). Motor fluctuations refer to a situation where the patients fluctuate between being in the ON state and the OFF state, with a tendency, as the PD progresses, to have an increase in time of being in the OFF state ('OFF time') and a decrease in time of being in the ON state ('ON time'). These can be dose-dependent and more predictable, or non-dose-dependent.

Because the effectiveness of levodopa can appear to decrease over longer periods of time, certain physicians prefer to commence treatment of PD with a dopamine agonist and/or monoamine oxidase inhibitor, reserving treatment with levodopa until later in the treatment sequence.

Levodopa is normally used together with an AADC inhibitor such as carbidopa or benserazide in order to reduce its peripheral metabolism and so reduce the dose required. It may also be used together with a COMT inhibitor, such as entacapone, to further reduce its peripheral metabolism and so further reduce the dose of levodopa required.

When evaluating the efficacy of known and candidate therapies for Parkinson's disease treated patients can be referred to as being in the ON or OFF states. Therapeutic benefit is thus established by an increase in ON time and/or a reduction in OFF time. An increase in ON time provides an increased duration of relief from symptoms. A decrease in OFF time provides for reduced periods of time in which PD patients undergoing therapy exhibit PD symptoms. Measure of ON and OFF time are conventionally established by observation, with the patient and/or physician keeping a diary of symptoms and their timings. The observed ON and OFF times in a treatment group can be compared with those in alternative treatment or placebo treated groups as appropriate to the clinical context. Methods used for these evaluations include the Unified Parkinson's Disease Rating Scale or UPDRS (see Fahn S. Unified Parkinson's disease rating scale. In Fahn S, Marsden CD, Goldstein M, and Calne DB (eds) Recent Developments in Parkinson's Disease. McMillan, 1987, New York) to follow the longitudinal course of PD and the MDS (Movement Disorder Society)-UPDRS (see .Goetz, et al (1 Jan. 2007). "Movement Disorder Society-sponsored revision of the Unified Parkinson's Disease Rating Scale (MDS-UPDRS): Process, format, and clinimetric testing plan". Movement Disorders 22 (1): 41-47). As known to those skilled in the art various other approaches can be used as deemed appropriate to establish clinical response, non-limiting examples of the approaches that might be applicable are PDQ-39 (Jenkinson et al, The Parkinson's disease questionnaire. User manual for the PDQ-39, PDQ-8 and PDQ Summary Index. Oxford: Health Services Research Unit, Department of Public Health, University of Oxford, 1998), NMSS (Chaudhuri et al., "The metric properties of a novel non-motor symptoms scale for Parkinson's disease: results from an international pilot study," Movement Disorders, vol. 22, no. 13, pp. 1901-1911, 2007), PDSS (Chaudhuri et al. The Parkinson's disease sleep scale: A new instrument for assessing sleep and nocturnal disability in Parkinson's disease. J Neurol Neurosurg Psychiatry 2002;73:629-35) Hoehn and Yahr staging and Schwab and England ADL scales http://neurosurgery.mgh.harvard.edu/functional/pdstages.htm). Safety assessments such as mMIDI (Grant JE. Impulse control disorders: A clinician's guide to understanding and treating behavioral addictions. New York: W.W. Norton & Company; 2008) and C-SSR (Posner et al. Columbia-Suicide Severity Rating Scale. *Am J Psychiatry*, 2011 168(12) 1266-1277 can also be used to establish clinical endpoints.

As noted above, as well as the symptoms of PD described above, PD patients in the course of their treatment can experience dyskinesia, a state where drug-induced involuntary muscle movements occur. Dyskinesia is not thought to be a symptom of PD itself but instead a side effect of the drugs used for the treatment of PD symptoms. Dyskinesia, for example resulting from high levels of levodopa, can occur during the ON state when the normal PD symptoms are otherwise under control. Levodopa-induced dyskinesia appears in patients who have taken levodopa for a prolonged period of time and generally occurs during the ON state although in late stage PD, dyskinesia can occur in OFF state.

Dyskinesia can be categorised into three main types. The most common form is peak-dose dyskinesia that occurs at peak levodopa levels and can be ameliorated by reducing the levodopa dose. A second form is diphasic dyskinesia occurring when levodopa levels are rising or falling and can also be ameliorated by reducing the levodopa dose. A third form of dyskinesia is OFF-time dystonia, these are sustained muscle contractions that cause, for example, twisting and repetitive movements or abnormal postures. These OFF-time dystonia correlate with akinesia (inability to initiate movement) when levodopa levels are low and are treatable with levodopa. A major challenge in the treatment of PD is to improve the PD patient's ON time (and/or conversely reduce the OFF time) without increasing the dyskinesia associated with PD therapy.

Late stage PD patients, classified as those patients who, after the initiation of levodopa therapy may i) suffer from an insufficient control of PD symptoms despite treatment with levodopa and/or ii) may suffer from motor complications such as motor fluctuations (which can be dose dependent or non-dose dependent) and dyskinesia. Delayed-ON is a prolongation of the time required for an anti-Parkinsonian drug effect to appear.

Dose-dependent (or predictable) motor complications are related to the time of dosing e.g. peak dose dyskinesias, end of dose (or wearing off) deterioration and biphasic dyskinesias. For less predictable motor complications (e.g. paroxysmal ON-OFF phenomenon, freezing), therapy intends to reduce the duration and/or intensity of OFF state. Hence, the main efficacy variable can be the decrease in the number, duration and/or intensity of OFF state. It should also be clear to what extent ON-time with dyskinesia and ON-time without dyskinesia is increased. In highly advanced PD, patients may suffer from severe and highly unpredictable and rapid motor fluctuations.

Therapies aimed to modify disease progression can either prevent or postpone late motor complications or fluctuations and/or delay disease progression. Ideally treatment should stop, or substantially reduce, further neurodegeneration and delay disease progression. However the mechanisms responsible for the dopaminergic cell loss in PD are unknown. No pharmacotherapy currently exists that has shown a relevant delay in disease progression.

For early untreated PD (de novo) patients a clinical goal to be achieved is to slow the progression of motor symptoms by assessing change in UPDRS.

For stable treated PD patients a clinical goal to be achieved is to slow further decline of motor impairment, prevent progression of disability, and prevent motor and non-motor complications. Key outcome measurements for this stage could be the emergence of so-called axial symptoms: e.g. freezing of gait, loss of balance or Hoehn and Yahr stage III ("bilateral disease: mild to moderate disability with impaired postural reflexes; physically independent" or "mild to moderate bilateral disease; some postural instability; physically independent").

For patients with advanced PD a clinical goal to be achieved is the prevention of disability. Clinical endpoints in this patent group are wide-ranging and include reductions in autonomic failure or falls, reduction of cognitive symptoms and possibly 'time to' dementia and 'time to' nursing home placement.

Combinations of carbidopa and levodopa are well known in the art, commercial examples of this combination with various release characteristics include Sinemet, Sinemet CR, Duodopa, Apodespan PR and Lecado.

Entacapone is a commercially available COMT inhibitor that has been clinically used in combination with carbidopa and levodopa for the treatment of PD. Entacapone is, for example, described in PCT publication nos WO0101984 (A1), WO0015196 (A1), WO2007090923 (A1), WO2006131591 (A2) and WO2011107653 (A2).

Recently, an improved COMT inhibitor termed opicapone (5-[3-(2,5-dichloro-4,6-dimethyl-1-oxy-pyridin-3-yl)-[1,2,4]oxadiazol-5-yl]-3-nitrobenzene-1,2-diol) has been employed in clinical trials together with levodopa and an AADC inhibitor such as carbidopa.

Opicapone is described inter alia in PCT/PT06/000020, PCT/PT2007/000016, PCT/PT2007/000043, PCT/PT2008/000042, PCT/PT2009/000044, PCT/PT2009/000013, PCT/PT2009/000009, PCT/PT2012/000048, PCT/PT2010/000014, PCT/PT2010/000015, PCT/GB2011/052056. Clinical trials of opicapone are described in Efficacy and Safety of BIA 9-1067 in Idiopathic Parkinson's Disease Patients; Efficacy and Safety of BIA 9-1067 in Idiopathic Parkinson's Disease Patients With "Wearing-off" Phenomenon; Pharmacokinetics of BIA 9-1067 and Its Metabolites in Healthy Male Elderly Subjects and in Healthy Male Young Subjects; Effect of Three Multiple-dose Regimens of BIA 9 1067 at Steady-state on the Levodopa Pharmacokinetics; Pharmacokinetic-pharmacodynamic Interaction Between Three Different Single Doses of BIA 9-1067 and a Single-dose of Immediate-release Levodopa/Benserazide; Pharmacokinetic-pharmacodynamic Interaction Between Three Different Single Doses of BIA 9-1067 and a Single-dose of Controlled-release 100/25 mg Levodopa/Benserazide; Pharmacokinetic-pharmacodynamic Interaction Between Each of Three Different Single Doses of BIA 9-1067 and a Single-dose of Controlled-release 100/25 mg Levodopa/Carbidopa; Comparative Bioavailability Study of BIA 9-1067 25 mg Capsules; Pharmacokinetics of BIA 9-1067 in Subjects With Hepatic Impairment; Pharmacokinetic-pharmacodynamic Interaction Between Each of Three Different Single Doses of BIA 9-1067 and a Single-dose of Immediate-release 100/25 mg Levodopa/Carbidopa; Effect of BIA 9-1067 on the Pharmacokinetics and Pharmacodynamics of Warfarin; Absorption, Distribution, Metabolism and Excretion of [14C]-Labeled BIA 9-1067 and Metabolites; Tolerability, Pharmacokinetics and Pharmacodynamics of BIA 9-1067; Effect of BIA 9-1067 on Rasagiline Pharmacokinetics; Effect of BIA 9-1067 on the Pharmacokinetics of Repaglinide; Effect of Rasagiline on BIA 9-1067 Pharmacokinetics; Pharmacokinetic Interaction Between BIA 9-1067 and Standard-release Levodopa/Carbidopa; Pharmacokinetics of BIA 9-1067 in Healthy Japanese and Caucasian Subjects; Effect of BIA 9-1067 at Steady-state on the Pharmacokinetics of Levodopa/Carbidopa and Levodopa/Benserazide; Effect of BIA 9-1067 on Cardiac Repolarization in Healthy Adult Men and Women; Study of BIA 9-1067 to Investigate Its Effect on Levodopa Pharmacokinetic; A Single Oral Ascending Dose Study of BIA 9-1067 in Healthy Male Subjects; A Study to Investigate the Tolerability and Effect of Three Single-dose Regimens of BIA 9-1067; The Effect of BIA 9-1067 at Steady-state on the Levodopa Pharmacokinetics; An Open-label Study in Healthy Male Subjects to Assess the Absorption, Distribution, Metabolism and Excretion of [14C]-Labelled BIA 9-1067 and Metabolites; Continuation Treatment Protocol for Patient Who Participated in the BIA 9-1067-302 Clinical Trial; Multicentre Study in Four Parallel Groups of Parkinson's Disease (PD) Patients. Details of these clinical trials can be found at http://clinicaltrials.gov.

THE INVENTION

FIGS. 1 and 2 disclose the use of opicapone together with levodopa and carbidopa or benserazide in patients not previously treated with the COMT inhibitor, opicapone (i.e. naïve to opicapone). When a comparison is made between patient groups naïve to opicapone and those previously treated with opicapone, it was observed that, for the patients treated with opicapone from an earlier stage, the PD had progressed less. When the results are analysed, it can be observed that PD had progressed less. The protocols by which patients were treated are provided in Example 1 herein and in the schematic in FIG. 3. The patients were treated with opicapone once a day. This dose was administered in the evening, at bedtime.

This is the first time that a treatment regimen has been shown to slow the progression of PD and so provides a significant development in therapy. As used herein slowing the progression of PD also refers to instances where the progression of PD is delayed by a period of time. For patient treated according to the invention the progression of PD may be delayed by a period of at least one month relative to patients who have not received the treatment of the invention, for example by at least 3 months, at least 4 months, at least 5 months, at least 6 months, at least 7 months, a least 9 months or at least one year.

Accordingly, the present invention provides a method of slowing or delaying the progression of PD by administering to a patient not previously treated with opicapone for at least a period of time before starting the administration:
(i) levodopa;
(ii) an AADC inhibitor such as carbidopa or benserazide; and
(iii) opicapone.

The present invention also provides the use of opicapone to slow the progression of PD by administering to a patient not previously treated with opicapone for at least a period of time before starting the administration:
(i) levodopa;
(ii) an AADC inhibitor such as carbidopa or benserazide; and
(iii) opicapone.

Alternative COMT inhibitors (COMTis) include tolcapone and entacapone.

Such period of time may be, for example, for 2 weeks, 1 month, 3 months, 6 months, 12 months, 18 months, or 24 months. The patient may never have taken opicapone before starting the treatment of the present invention. Any of the medicaments set forth above in (i), (ii) and (iii) may be present as a pharmaceutically acceptable salt or ester, if desired. The medicaments may be administered separately (concomitantly or sequentially), or in a fixed dose combination of two or more of (i), (ii) and (iii). When in a fixed-dose combination, the release of one or more of the medicaments may be modified to provide rapid, sustained and/or delayed release of one or more of the medicaments. Such rapid release forms may be immediate release forms.

The patient to be treated according to the invention may have previously been experiencing a mean daily OFF time of up to 6 hours prior to treatment according to the invention, for example up to 1 hour, up to 2 hours, up to 3 hours, up to 4 hours, or up to 5 hours per day. Such patients may have had a PD diagnosis for up to 9 years, for example up to 1 month, up to 2 months, up to 3 months, up to 4 months, up to 6 months, up to 12 months, up to 2 years, up to 3 years, up to 4 years, up to 5 years, up to 6 years, up to 7 years or up to 8 years. The patients to be treated according to the invention may have previously been experiencing motor symptoms and/or motor complications such as motor fluctuations with or without dyskinesias for up to 4 years prior to treatment according to the invention, for example up to 1 month, up to 2 months, up to 3 months, up to 4 months, up to 6 months, up to 12 months, up to 2 years, or up to 3 years. The patients to be treated according to the invention may have previously been taking an average daily dose of levodopa of up to 800 mg prior to treatment according to the invention, for example up to 700 mg, up to 600 mg, up to 500 mg, up to 400 mg, up to 300 mg, up to 200 mg, or up to 100 mg. In such patients administered with opicapone according to the invention the OFF time will decrease and the daily dosing of levodopa may decrease, at least initially.

The opicapone may be employed by once a day dosing, for example at 5 mg to 100 mg, more usually 25 mg to 75 mg, for example 50 mg per day. Individual doses of 5 mg, 7.5 mg, 10 mg, 12.5 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg or the like may be employed (or such a dose at 10%).

The opicapone may be administered at any time but more suitably not at or near mealtime, and/or more suitably not together with levodopa or near administration thereof. Particularly aptly the opicapone is administered in the evening, for example at least an hour before or after a meal and at least an hour before or after the last administration of levodopa, for example before going to bed (at bedtime). Suitable administration is described in PCT/GB2011/052056.

The dosage unit for opicapone may be a tablet, a capsule or the like. Administration is usually and preferably oral.

The opicapone, levodopa and AADC inhibitor (such as carbidopa or benserazide) will be administered in an amount effective to treat Parkinson's disease in a patient in need thereof.

The levodopa and AADC inhibitor will usually be administered at the same time as each other, for example as a single dosage unit such as a tablet. The single dosage may include a fixed dose combination unit. Alternatively, part or all of the AADC inhibitor may be administered separately if desired.

The dose of levodopa will normally be from 50 mg to 250 mg, more usually from 95 mg to 200 mg, for example 100 mg or 150 mg.

The dose of AADC inhibitor may conventionally be in a ratio of 1:4 with levodopa, for example 25 mg benserazide or carbidopa together with 100 mg levodopa. Higher doses of AADC inhibitor may be employed if desired, for example co-formulated with the levodopa although additional doses such as tablet(s), for example of 25 mg carbidopa, may be employed.

The levodopa may be administered from, for example, 2 to 10 times a day in order to minimise the patients symptoms thereby minimising the patient's end-of-dose wearing off symptoms and "off-time". Generally 3, 4, 5, 6, 7 or 8 times a day is employed, for example 3, 4 or 5 times a day.

ease and end-of-dose motor fluctuations in combination with immediate release or modified release preparations of levodopa/benserazide or levodopa/carbidopa wherein the end-of-dose motor fluctuations cannot be stabilised by the preparations of levodopa/benserazide or levodopa/carbidopa alone is therefore also envisaged.

Suitable dosages and combinations are described in Table 1:

TABLE 1

Combination of opicapone with levodopa/AADCi, levodopa/AADCi/COMTi and AADCi preparations.

| Combinations with opicapone | Capsules/Tablets/Other Immediate Release (IR)/ Controlled Release (CR) | Dosage(s) (mg/mg) | Administration regime(s) |
|---|---|---|---|
| Levodopa/AADCi preparations | | | |
| Levodopa/Carbidopa | IR | 50/12.5 100/10 100/25 250/25 | 400-1600 mg of L-DOPA and carbidopa 100-650 mg daily in divided doses (2 to 10 doses per day, for example, 2, 3, 4, 5, 6, 7, 8, 9 or 10 doses a day) |
| | Orally Disintegrating | 100/10 100/25 250/25 | |
| | CR | 200/50 100/25 | |
| | Intestinal Gel | 20/5 | |
| Levodopa/Benserazide | Capsules/Tablets | 50/12.5 100/25 200/50 | 400-1600 mg of levodopa and benserazide 100-650 mg daily in divided doses (2 to 10 doses per day, for example, 2, 3, 4, 5, 6, 7, 8, 9 or 10 doses a day) |

When opicapone is used in combination with levodopa and carbidopa, a daily dose of levodopa from 400 mg to 1600 mg and carbidopa from 100 to 650 mg can used. In this case the daily dose of levodopa and carbidopa is provided in 2 to 10 doses per day, for example, 2, 3, 4, 5, 6, 7, 8, 9 or 10 doses a day.

When opicapone is used in combination with levodopa and benserazide, a daily dose of levodopa from 400 mg to 1600 mg and benserazide from 100 to 650 mg can be used. In this case the daily dose of levodopa and benserazide is provided in 2 to 10 doses per day, for example, 2, 3, 4, 5, 6, 7, 8, 9 or 10 doses a day.

Use of opicapone with an agent delivering a pharmacologically equivalent dose of levodopa and/or the AADC inhibitors detailed above is also envisaged.

Opicapone may be indicated as adjunctive therapy to preparations of levodopa/benserazide or levodopa/carbidopa in adult patients with Parkinson's disease and motor fluctuations. Use of opicapone for the treatment of (or method of treating) Parkinson's disease in adult patients with Parkinson's disease and motor fluctuations in combination with preparations of levodopa/benserazide or levodopa/carbidopa is therefore also envisaged.

Opicapone may be indicated as adjunctive therapy to immediate release or modified release preparations of levodopa/benserazide or levodopa/carbidopa in adult patients with Parkinson's disease and end-of-dose motor fluctuations who cannot be stabilised on those combinations. Use of opicapone for the treatment of (or method of treating) Parkinson's disease in adult patients with Parkinson's dis- A particularly apt dosage of levodopa is 100 mg levodopa and 25 mg AADC inhibitor (AADCi) particularly carbidopa.

It is a further advantage of this invention that control of dyskinesias may be achieved. This may be due at least in part to the association of the use of opicapone administered, for example, once a day, together with a dose of levodopa such as 100 mg.

Favourably the levodopa is present in a rapidly dissolving tablet although sustained release forms may be employed. The levodopa may also be used in delayed or immediate release forms.

In one suitable embodiment, the treatment is administered to a patient not previously treated with a COMT inhibitor such as entacapone, tolcapone or opicapone for at least a period of time before starting the treatment of the present invention. Such period of time may be, for example, for 2 weeks, 1 month, 3 months, 6 months, 12 months, 18 months, or 24 months. The patient to be treated according to the invention may never have taken a COMT inhibitor before starting the treatment of the present invention. Such patients to be treated according to the invention may have previously been experiencing a mean daily OFF time of up to 6 hours prior to treatment according to the invention, for example up to 1 hour, up to 2 hours, up to 3 hours, up to 4 hours, or up to 5 hours per day. Such patients to be treated according to the invention may have had a PD diagnosis for up to 9 years prior to treatment according to the invention, for example up to 1 month, up to 2 months, up to 3 months, up to 4 months, up to 6 months, up to 12 months, up to 2 years, up to 3 years, up to 4 years, up to 5 years, up to 6 years, up to 7 years or up to 8 years. The patients to be treated according to the invention may have been experiencing motor symptoms and/or motor complications such as motor fluctuations with or without dyskinesias for up to 4 years prior to treatment according to the invention, for example up to 1 month, up to 2 months, up to 3 months, up to 4 months, up to 6 months, up to 12 months, up to 2 years, or up to 3 years. The patients to be treated according to the invention may be taking an average daily dose of levodopa of up to 800 mg prior to treatment according to the invention, for example up to 700 mg, up to 600 mg, up to 500 mg, up to 400 mg, up to 300 mg, up to 200 mg, or up to 100 mg.

In another suitable embodiment, there is provided a method of slowing progression of PD in a patient previously treated with an effective dose of levodopa and an AADC inhibitor which comprises administering an effective dose of opicapone to said patient. In such cases the AADC inhibitor can be carbidopa or benserazide.

In another suitable embodiment there is opicapone for use delaying the progression of PD in a patient also treated with levodopa and an AADC inhibitor. In such cases the AADC inhibitor can be carbidopa or benserazide.

Such patients to be treated according to the invention may have been experiencing a mean daily OFF time of up to 6 hours prior to treatment according to the invention, for example up to 1 hour, up to 2 hours, up to 3 hours, up to 4 hours, or up to 5 hours per day. Such patients to be treated according to the invention may have had a PD diagnosis for up to 9 years, for example up to 1 month prior to treatment according to the invention, up to 2 months, up to 3 months, up to 4 months, up to 6 months, up to 12 months, up to 2 years, up to 3 years, up to 4 years, up to 5 years, up to 6 years, up to 7 years or up to 8 years. The patients to be treated according to the invention may have been experiencing motor symptoms and/or motor complications such as motor fluctuations with or without dyskinesias for up to 4 years prior to treatment according to the invention, for example up to 1 month, up to 2 months, up to 3 months, up to 4 months, up to 6 months, up to 12 months, up to 2 years, or up to 3 years. The patients to be treated according to the invention may have been taking an average daily dose of levodopa of up to 800 mg prior to treatment according to the invention, for example up to 700 mg, up to 600 mg, up to 500 mg, up to 400 mg, up to 300 mg, up to 200 mg, or up to 100 mg.

The opicapone may be employed by once a day dosing, for example at 5 mg to 100 mg, more usually 25 mg to 75 mg, for example 50 mg per day. Individual doses of 5 mg, 7.5 mg, 10 mg, 12.5 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg or the like may be employed (or such a dose at 10%).

The opicapone may be administered at any time but more suitably not at or near mealtime, and/or more suitably not together with levodopa or near administration thereof. Particularly aptly the opicapone is administered in the evening, for example at least an hour before or after a meal and at least an hour before or after the last administration of levodopa, for example before going to bed (at bedtime). Suitable administration is described in PCT/GB2011/052056.

The dosage unit for opicapone may be a tablet, a capsule or the like. Administration usually and preferably oral.

In another suitable embodiment there is provided a method of slowing or delaying progression of PD in a patient diagnosed with, but previously untreated for, Parkinson's disease which comprises administering an effective dose of opicapone to said patient. The invention also provides the use of opicapone for slowing or delaying progression of PD in a patient diagnosed with, but previously untreated for, Parkinson's disease which comprises administering an effective dose of opicapone to said patient. For example, use of opicapone in the treatment of the symptoms of idiopathic PD without or in combination with levodopa, i.e. over the course of the disease, including through to late stages when the effect of levodopa wears off or becomes inconsistent and fluctuations of the therapeutic effect occur (end of dose or ON-OFF fluctuations As described herein a patient previously untreated for PD includes those PD patients who have not previously taken medication for treatment of PD. Medication for treatment of PD is described in Table 2 and includes dopamine agonists, dopamine precursors such as levodopa, COMT inhibitors, MAO-B inhibitors, and anti-cholinergics. Before commencing treatment according to the invention such patients may experience a mean daily OFF time of up to 6 hours, for example up to 1 hour, up to 2 hours, up to 3 hours, up to 4 hours, or up to 5 hours per day. Before commencing treatment according to the invention such patients may have had a PD diagnosis for up to 9 years, for example up to 1 month, up to 2 months, up to 3 months, up to 4 months, up to 6 months, up to 12 months, up to 2 years, up to 3 years, up to 4 years, up to 5 years, up to 6 years, up to 7 years or up to 8 years. Before commencing treatment according to the invention the patients may experience motor symptoms and/or motor complications such as motor fluctuations with or without dyskinesias for up to 4 years, for example up to 1 month, up to 2 months, up to 3 months, up to 4 months, up to 6 months, up to 12 months, up to 2 years, or up to 3 years.

TABLE 2

Parkinson's Disease Medication

Part A

| Drug Type | Capsules/Tablets/Other Immediate Release (IR)/ Controlled/Extended Release (CR/ER) | Dosage(s) (mg) | Administration regime(s) |
|---|---|---|---|
| Dopamine agonists | | | |
| Pramipexole | Conventional tablets | 0.125 mg | TID (1.5-4.5 mg daily) |
| | | 0.25 mg | |
| | | 0.5 mg | |
| | | 0.75 mg | |
| | | 1 mg | |
| | | 1.5 mg | |

TABLE 2-continued

Parkinson's Disease Medication

| | | | |
|---|---|---|---|
| | Extended release | 0.375 mg | QD (1.5-4.5 mg daily) |
| | | 0.75 mg | |
| | | 1.5 mg | |
| | | 2.25 mg | |
| | | 3 mg | |
| | | 3.75 mg | |
| | | 4.5 mg | |
| Ropinirole | Conventional tablets | 0.25 mg | TID (2-24 mg daily) |
| | | 0.5 mg | |
| | | 1 mg | |
| | | 2 mg | |
| | | 3 mg | |
| | | 4 mg | |
| | | 5 mg | |
| | Extended release tablets | 2 mg | QD (2-24 mg daily) |
| | | 4 mg | |
| | | 6 mg | |
| | | 8 mg | |
| | | 12 mg | |
| Rotigotine | Transdermal system | 1 mg | QD (2-8 mg daily) |
| | | 2 mg | |
| | | 3 mg | |
| | | 4 mg | |
| | | 6 mg | |
| | | 8 mg | |
| Apomorphine | Ampoules - Solution for Injection or Infusion | 10 mg/ml | 2 mg PRN, up to 20 mg/day |
| | Pen - Solution for Injection Pre-filled Syringe - solution for infusion | 5 mg/ml | Continuous infusion 12-24 h/day |
| Bromocriptine | Tablets | 1 mg | TID (5-30 mg daily) |
| | | 2.5 mg | |
| | Capsules | 5 mg | |
| | | 10 mg | |
| Lisuride | Tablets | 0.2 mg | BID or TID (0.6-5 mg daily) |
| Pergolide | Tablets | 0.05 mg | TID (0.75-5 mg daily) |
| | | 0.25 mg | |
| | | 1 mg | |
| Cabergoline | Tablets | 0.5 mg | QD (2-4 mg daily) |
| Budipine | Tablets | 10 mg | |
| | | 20 mg | |
| | | 30 mg | |
| Piribedil | Tablets | 20 mg | 20 mgTID |
| | | 50 mg Retard | 50 mgQD |
| Talipexole | Tablets | 0.4 mg | BID or TID (0.4-3.6 mg daily) |
| Dopamine precursors | | | |
| Levodopa-carbidopa | See Part B | See Part B | |
| Levodopa-benserazide | See Part B | See Part B | |
| Levodopa-carbidopa-entacapone | See Part B | See Part B | |
| COMT inhibitors | | | |
| Entacapone | Tablets | 200 mg | 200 mg up to ten times daily |
| Entacapone-levodopa-carbidopa | See Part B | See Part B | |
| Tolcapone | Tablets | 100 mg | TID |
| | | 200 mg | |
| MAO-B inhibitors | | | |
| Selegiline | Tablets/Capsules | 5 mg | 5 mg BID |
| | | 10 mg | 10 mg QD |
| | Syrup | 10 mg/5 ml | |
| | Orally Disintegrating Tablets | 1.25 mg | 1.25 QD |
| Rasagiline | Tablets | 0.5 mg | QD |
| | | 1 mg | |
| Other drugs | | | |
| Amantadine | Capsules/Tablets | 100 mg | 100-400 mg QD |
| | Syrup | 50 mg/5 ml | |
| Anticholinergics | | | |
| Trihexylphenidyl (benzhexol) | Tablets | 2 mg | TID (6-8 mg daily) |
| | | 5 mg | |
| | Elixir | 2 mg/5 ml | |
| Biperiden | Tablets | 2 mg | 3-16 mg daily in divided doses |
| | | 4 mg | |

TABLE 2-continued

Parkinson's Disease Medication

| Benztropine | Tablets | 0.5 mg | 4-6 mg daily in divided doses |
|---|---|---|---|
| | | 1 mg | |
| | | 2 mg | |
| | Injection IM IV | 2 mg/ml | |
| Procyclidine | Tablets | 5 mg | 2.5-5 mg TID |
| Orphenadrine | Injection IM | 30 mg/ml | 60 mg BID |

Part B

| Combinations | Capsules/Tablets/Other Immediate Release (IR)/ Controlled Release (CR) | Dosage(s) (mg) | Administration regime(s) |
|---|---|---|---|
| Levodopa/AADCi | | | |
| Levodopa-Carbidopa | IR | 50/12.5 | 400-1600 mg of levodopa in divided do |
| | | 100/10 | |
| | | 100/25 | |
| | | 250/25 | |
| | Orally Disintegrating | 100/10 | |
| | | 100/25 | |
| | | 250/25 | |
| | CR | 200/50 | |
| | | 100/25 | |
| | Intestinal Gel | 20/5 | |
| Levodopa-Benserazide | Capsules/Tablets | 50/12.5 | |
| | | 100/25 | |
| | | 200/50 | |
| | Dispersible Tablets | 50/12.5 | |
| | | 100/25 | |
| | Controlled release | 100/25 | |
| Levodopa/AADCi/COMTi | | | |
| Levodopa-carbidopa-Entacapone | | 50/12.5/200 | |
| | | 75/18.75/200 | |
| | | 100/25/200 | |
| | | 125/31.25/200 | |
| | | 150/37.5/200 | |
| | | 200/50/200 | |

TID—three times per day
BID—twice per day
QD—once per day

The patient to be treated for Parkinson's disease may have been previously treated with L-DOPA. The patient to be treated for Parkinson's disease may not have been previously treated with L-DOPA. The patient to be treated for Parkinson's disease may have been previously treated with a dopamine agonist or MAO-B inhibitor such as set out above. The patient to be treated for Parkinson's disease may not have been previously treated with a dopamine agonist or MAO-B inhibitor. The patient to be treated for Parkinson's disease may not have been previously treated for Parkinson's disease.

In another suitable embodiment the treatment according to the invention is administered to a patient not previously treated with levodopa for at least a period of time before starting the treatment of the present invention. Such period of time may be, for example, for 2 weeks, 1 month, 3 months, 6 months, 12 months, 18 months, or 24 months. The patient to be treated according to the invention may never have taken levodopa before starting the treatment of the present invention.

The opicapone may be employed by once a day dosing, for example at 5 mg to 100 mg, more usually 25 mg to 75 mg, for example 50 mg per day. Individual doses of 5 mg, 7.5 mg, 10 mg, 12.5 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg or the like may be employed (or such a dose at 10%).

The opicapone may be administered at any time but more suitably not at or near mealtime, and/or more suitably not together with levodopa or near administration thereof. Particularly aptly the opicapone is administered in the evening, for example at least an hour before or after a meal and at least an hour before or after the last administration of levodopa, for example before going to bed (at bedtime). Suitable administration is described in PCT/GB2011/052056.

The dosage unit for opicapone may be a tablet, a capsule or the like. Administration is usually and preferably oral.

The progression of Parkinson's Disease may be determined by noting the change in any PD symptom or commonly used measure of PD symptoms (see Examples 1A and 1B), for example, OFF time and/or ON time, for example a reduction in OFF time compared to starting the treatment of the invention and/or an increase in ON time compared to starting the treatment of the invention. The reduction in OFF time could suitably be of at least 10 minutes. The reduction in OFF time by at least 10 minutes can be for example at least 15 minutes, at least 30 minutes, at least 45 minutes or at least an hour, for example between 15 minutes and 30 minutes, between 30 minutes and an hour. A corresponding relative improvement in ON time may similarly be employed to determine progression of disease. As shown in FIG. 1, at least 12 months post commencement of treatment with opicapone, a difference of approximately −2.0 hrs in OFF time is seen. As shown in FIG. 2, at least 12 months post commencement of treatment with opicapone a difference of approximately +1.5 hr in ON time without troublesome dyskinesia is seen.

EXAMPLE 1A

Figure 3:
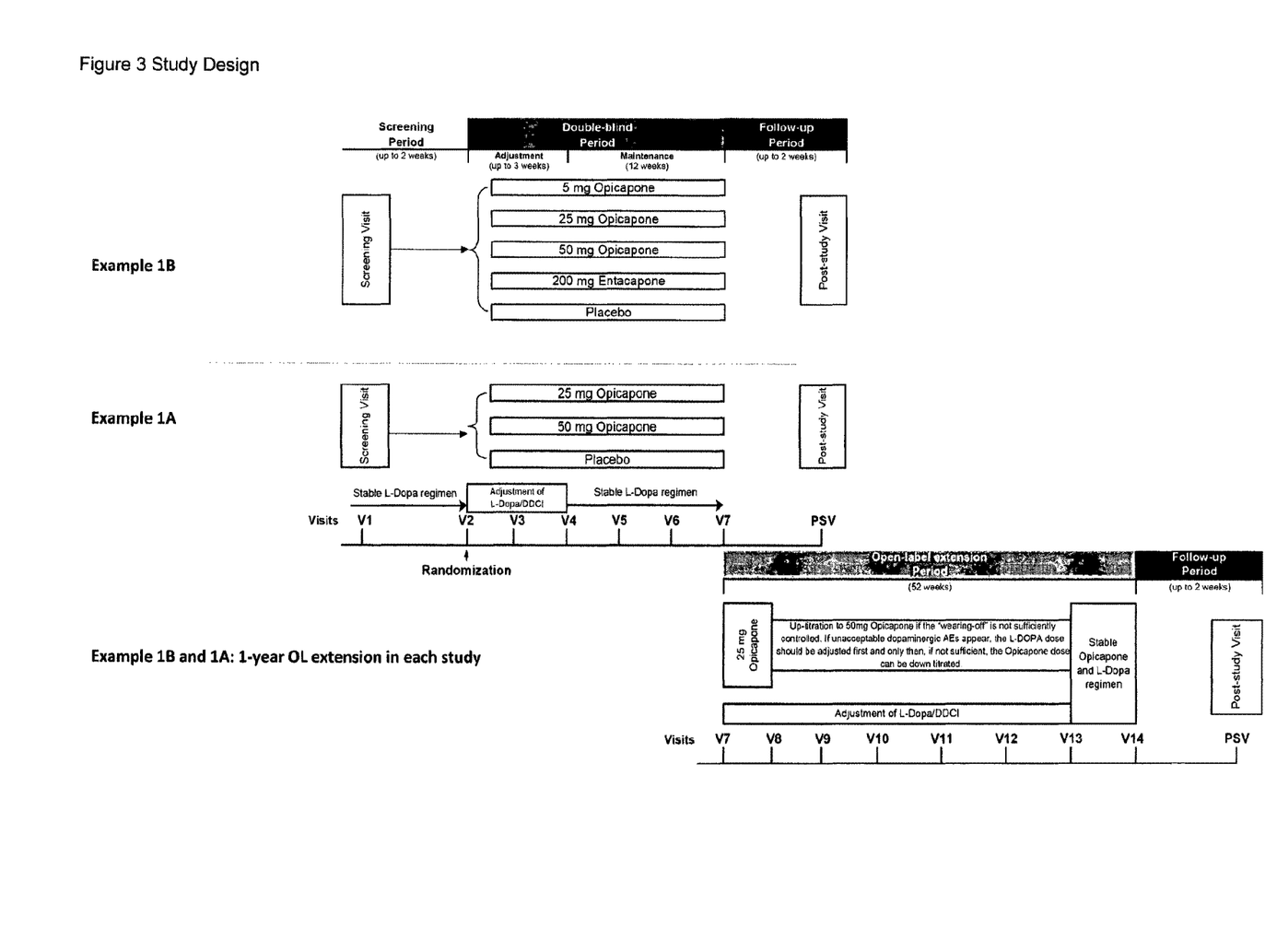

After completion of the placebo-controlled double-blind (DB) trial—see FIG. 3, 367 (97.6%) patients continued to a 1-year open label (OL)-part, in which all subjects were treated with OPC (25 or 50-mg OPC). All subjects began with 25-mg OPC once daily (QD) for 1-week. Then, the investigator freely adjusted the levodopa therapy and/or OPC based on the dopaminergic response and/or associated adverse events. Efficacy variables included the change from baseline in OFF/ON-time, based on patient diaries. Other endpoints include proportion of responders. UPDRS, PD questionnaire (PDQ-39), Non-Motor Symptom Scale (NMSS), PD Sleep Scale (PDSS) and safety assessments (including Columbia Suicide Severity Rating Scale (C-SSRS). Modified Minnesota Impulsive Disorders Interview (mMIDI)) was also employed.

EXAMPLE 1B

After completion of the placebo-controlled double-blind (DB) trial—see FIG. 3, 495 (92%) patients continued to a 1-year open label (OL)-part, in which all subjects were treated with OPC (5, 25 or 50-mg OPC). All subjects began with 25-mg OPC QD for 1-week. Then, the investigator freely adjusted the levodopa therapy and/or OPC based on the dopaminergic response and/or associated adverse events. Efficacy variables included the change from baseline in OFF/ON-time, based on patient diaries. Other endpoints include proportion of responders. UPDRS, PDQ-39, NMSS, PDSS and safety assessments (including C-SSRS and mMIDI).

The data from the trials is shown in FIGS. 1 and 2.

The demographic details of the patients at baseline of the double blind portion of the study in Example 1A is presented in Table 3 below. The demographic details of the patients at baseline of the open label extension period of the study in Example 1A is presented in Table 4.

TABLE 3

Demographic details of PD patients on entry to the double blind study of Example 1A.

|  |  | Placebo (N = 120) | 25 mg OPC (N = 116) | 50 mg OPC (N = 115) |
|---|---|---|---|---|
| Age (yrs) | Mean (SD) | 61.5 (8.9) | 62.5 (8.5) | 65.5 (8.4) |
| Gender |  |  |  |  |
| Male | n (%) | 71 (52.6) | 82 (65.6) | 89 (60.5) |
| Female | n (%) | 64 (47.4) | 43 (34.4) | 58 (39.5) |
| Race |  |  |  |  |
| Asian | n (%) | 42 (31.1) | 29 (23.2) | 31 (21.1) |
| Caucasian | n (%) | 89 (65.9) | 90 (72.0) | 115 (78.2) |
| Neither Asian or caucasian | n (%) | 3 (2.2) | 6 (4.8) | 1 (0.7) |
| Weight (kg) | Mean (SD) | 72 (7.0) | 75 (16.8) | 72 (15.1) |
| Body Mass Index (kg/m$^2$) | Mean (SD) | 27 (5.2) | 27 (4.9) | 26 (4.3) |
| Time since |  |  |  |  |
| PD diagnosis (yrs) | Mean (SD) | 7.7 (3.7) | 8.5 (4.4) | 8.2 (4.6) |
| Motor fluctuations (yrs) | Mean (SD) | 3.6 (2.7) | 3.8 (2.8) | 3.6 (3.5) |
| L-DOPA treatment (yrs) | Mean (SD) | 6.7 (3.6) | 7.1 (4.2) | 7.0 (4.7) |
| OFF-time (hrs) | Mean (SD) | 6.1 (2.3) | 6.2 (2.2) | 6.3 (2.2) |
| L-DOPA Daily-dose (mg) | Mean (SD) | 714 (337.5) | 806 (398.2) | 700 (311.9) |

TABLE 4

Demographic details of opicapone (OPC) treated PD Patients on entry to the open label extension period of the study of Example 1A.

| Characteristic | Statistic | OPC (N = 339) |
|---|---|---|
| Age (years) | Mean (SD) | 63 (9) |
| Gender |  |  |
| Male | n (%) | 201 (59.3%) |
| Female | n (%) | 138 (40.7%) |
| Race |  |  |
| Asian | n (%) | 238 (70.2%) |
| Caucasian | n (%) | 91 (26.8%) |
| Neither Asian nor Caucasian | n (%) | 10 (2.9%) |
| Levodopa daily dose (mg) | Mean (SD) | 707.3 (334.3) |
| OFF-time (hours) | Mean (SD) | 4.5 (3.0) |

SD = standard deviation

The demographic details of the patients at baseline of the double blind portion of the study in Example 1B is presented in Table 5 below. The demographic details of the patients at baseline of the open label extension period of the study in Example 1B is presented in Table 6. Table 5 Demographic details of PD patients on entry to the double blind study of Example 1B. SD=standard deviation

|  |  | Placebo (N = 121) | Entacapone (N = 122) | 5 mg OPC (N = 122) | 25 mg OPC (N = 119) | 50 mg (N = 115) |
| --- | --- | --- | --- | --- | --- | --- |
| Age (yrs) | Mean (SD) | 64 (9.3) | 64 (8.8) | 64 (9.3) | 64 (8.9) | 64 (9.2) |
| Gender |  |  |  |  |  |  |
| Male | n (%) | 71 (58.7%) | 76 (62.3%) | 71 (58.2%) | 67 (56.3%) | 69 (60.0%) |
| Female | n (%) | 50 (41.3%) | 46 (37.7%) | 51 (41.8%) | 52 (43.7%) | 46 (40.0%) |
| Race |  |  |  |  |  |  |
| Caucasian | n (%) | 121 (100) | 122 (100) | 122 (100) | 119 (100) | 115 (100) |
| Weight (kg) | Mean (SD) | 76 (13.3) | 77 (15.0) | 75 (12.0) | 76 (14.1) | 76 (14.5) |
| Body Mass Index (kg/m$^2$) | Mean (SD) | 27 (4.3) | 27 (4.6) | 26 (4.5) | 27 (4.3) | 27 (4.6) |
| Time since: |  |  |  |  |  |  |
| PD diagnosis (yrs) | Mean (SD) | 7.7 (4.2) | 7.1 (4.1) | 7.5 (3.6) | 7.2 (4.1) | 7.0 (3.8) |
| Motor fluctuations (yrs) | Mean (SD) | 2.2 (1.9) | 2.2 (2.1) | 2.3 (2.3) | 2.3 (2.5) | 2.2 (2.3) |
| L-DOPA treatment (yrs) | Mean (SD) | 5.8 (3.7) | 5.6 (4.1) | 5.8 (3.5) | 5.9 (3.9) | 5.3 (3.8) |
| OFF-time (hrs) | Mean (SD) | 6.2 (1.8) | 6.5 (2.2) | 6.7 (2.1) | 6.9 (2.2) | 6.2 (1.8) |
| L-DOPA Daily-dose (mg) | Mean (SD) | 675 (302.1) | 645 (329.7) | 642 (310.3) | 654 (324.3) | 695 (337.5) |

TABLE 6

Demographic details of opicapone (OPC) treated PD Patients on entry to the open label extension period of the study of Example 1B.

| Characteristic | Statistic | OPC (N = 339) |
| --- | --- | --- |
| Age (years) | Mean (SD) | 64 (9) |
| Gender |  |  |
| Male | n (%) | 298 (60.3%) |
| Female | n (%) | 196 (39.7%) |
| Race |  |  |
| Caucasian | n (%) | 494 (100%) |
| Levodopa daily dose (mg) | Mean (SD) | 649.4 (307.5) |
| OFF-time (hours) | Mean (SD) | 4.9 (2.6) |

SD = standard deviation

EXAMPLE 2

Introduction: Opicapone (OPC) was developed to fulfil the need for more potent, safer and longer acting COMT inhibitors.

Objectives: To investigate the effect of a once-daily (QD) OPC (25, 50 and 75 mg) on levodopa pharmacokinetics (PK), in comparison to placebo and 200 mg entacapone (ENT).

Methods: This was a single-centre, double-blind, randomized and placebo-controlled study in 4-groups of 20 (10 male and 10 female) subjects each. The study consisted of QD administration of OPC or placebo for 11 days followed by thrice-daily (every 5 h) 100/25 mg levodopa/carbidopa (LC), 200 mg ENT or placebo on Day 12.

Results: Levodopa extent of exposure (AUC) was significantly increased up to 78.9% and 73.7% with 75 mg-OPC in comparison to placebo and ENT, respectively. Levodopa-AUC0-24 was higher when LC was administered with any OPC dose than when administered concomitantly with ENT. Peak exposure (Cmax) to levodopa increased (>30%) with 75 mg-OPC following LC administrations. A significantly long-lasting and sustained S-COMT inhibition occurred with OPC. Maximum S-COMT inhibition ranged from 67.1% (200 mg-ENT) to 94.2% (75 mg-OPC) and was higher than ENT for all OPC doses. The 50 and 75 mg-OPC were somehow similar (75 mg was slightly superior); thus, the 75 mg-OPC may not bring a significant advantage to 50 mg-OPC with regard to S-COMT inhibition. The tolerability profile of OPC was favourable.

The invention claimed is:

1. A method of slowing progression of Parkinson's Disease which comprises administering to a patient not previously treated with a COMT inhibitor an effective amount of:
   (i) levodopa;
   (ii) an AADC inhibitor; and
   (iii) opicapone, wherein the dose of opicapone is 15 mg to 100 mg once per day;
   wherein the patient not previously treated with a COMT inhibitor refers to a patient
      (1) experiencing a mean daily OFF time of up to 6 hours;
      (2) having a PD diagnosis for up to 8 years;
      (3) experiencing motor symptoms and/or motor complications for up to 4 years; or
      (4) taking an average daily dose of levodopa of up to 800 mg.

2. The method of claim 1, wherein the COMT inhibitor is opicapone.

3. The method of claim 1, wherein the patient has not previously been treated with levodopa.

4. The method of claim 1, wherein the slowing of the progression of Parkinson's Disease involves a delay in the progression of Parkinson's Disease by a period of at least one month.

5. The method of claim 1, wherein opicapone is administered once a day and levodopa is administered from 2 to 10 times a day.

6. The method of claim 1, wherein the dose of opicapone is 25 mg to 100 mg.

7. The method of claim 1, wherein the AADC inhibitor is carbidopa or benserazide.

8. The method of claim 1, wherein the levodopa is present in a unit dose of from 50 mg to 250 mg.

9. The method of claim 1, wherein the levodopa is present in a tablet at 100 mg.

10. The method of claim 1, wherein the AADC inhibitor is carbidopa or benserazide, wherein the levodopa and the AADC inhibitor are present in a single dosage unit.

11. The method of claim 10, wherein the single dosage unit is a tablet comprising 100 mg levodopa and 25 mg carbidopa for use 3, 4, 5 or 6 times a day and opicapone 50 mg for use once a day.

12. The method of claim 1, wherein the method is the first treatment provided to the patient for treatment of Parkinson's Disease.

13. The method of claim 1, wherein the patient benefits by more than 0.25 hr in OFF period.

14. The method of claim 1, wherein the patient has previously been treated for Parkinson's disease with a dopamine agonist or MAO-B inhibitor.

15. The method of claim 1, wherein the patient has not previously been treated for Parkinson's disease with a dopamine agonist or MAO-B inhibitor.

16. A method of delaying progression of Parkinson's Disease in patients treated with an effective dose of levodopa and an AADC inhibitor which comprises administering an effective dose of opicapone to said patient,
    wherein the dose of opicapone is 15 mg to 100 mg once per day;
    wherein the patient refers to a patient
        (1) experiencing a mean daily OFF time of up to 6 hours;
        (2) having a PD diagnosis for up to 8 years;
        (3) experiencing motor symptoms and/or motor complications for up to 4 years; or
        (4) taking an average daily dose of levodopa of up to 800 mg.

17. The method of claim 16, wherein opicapone is administered once a day, wherein the dose of opicapone is 25 mg to 100 mg.

18. The method of claim 17, wherein the dose of opicapone is 50 mg.

19. The method of claim 16, wherein levodopa is administered 3, 4, 5 or 6 times a day, wherein levodopa is present in a unit dose of from 50 mg to 250 mg.

20. The method of claim 16, wherein the AADC is carbidopa or benserazide in a ratio of 1:4 with levodopa.

21. The method of claim 19, wherein levodopa is used at 100 mg and carbidopa at 25 mg.

* * * * *